United States Patent [19]

Booth et al.

[11] Patent Number: 4,804,849
[45] Date of Patent: Feb. 14, 1989

[54] METHOD AND APPARATUS FOR DETERMINING CONCENTRATIONS OF CHLOROPHYLL AND THE RATE OF PRIMARY PRODUCTION IN WATER

[75] Inventors: Charles R. Booth, San Diego; Dale A. Kiefer, Los Angeles, both of Calif.

[73] Assignee: Biospherical Instruments Inc., San Diego, Calif.

[21] Appl. No.: 3,755

[22] Filed: Jan. 16, 1987

[51] Int. Cl.[4] .......................................... G01N 21/62
[52] U.S. Cl. .............................. 250/459.1; 250/458.1; 356/221; 356/417
[58] Field of Search ............... 250/458.1, 461.1, 461.2, 250/459.1; 356/221, 225, 317, 318, 417

[56] References Cited

U.S. PATENT DOCUMENTS

| | | | |
|---|---|---|---|
| 3,666,945 | 5/1972 | Früngel et al. | 250/461.1 |
| 4,084,905 | 4/1978 | Schreiber et al. | 250/458.1 |
| 4,178,101 | 12/1979 | Booth | 356/221 |
| 4,178,512 | 12/1979 | Früngel et al. | 250/461.1 |
| 4,293,225 | 10/1981 | Wheaton et al. | 250/461.1 |
| 4,650,336 | 3/1987 | Moll | 250/458.1 |

FOREIGN PATENT DOCUMENTS 0071991 2/1983 European Pat. Off. ......... 250/461.2

OTHER PUBLICATIONS

Leblanc et al., "Laser Spectrofluorimetry of Chlorophylls", Biophysics Research Project, University of Quebec, pp. 3723–3727, 6/1974.

Primary Examiner—Janice A. Howell
Assistant Examiner—William F. Rauchholz
Attorney, Agent, or Firm—Baker, Maxham & Jester

[57] ABSTRACT

Apparatus is provided for optically measuring scalar irradiance or incident flux of radiant energy and for optically measuring naturally occurring chlorophyll fluorescence or upwelling radiance in a parcel of water in a natural setting. From a comparison of the two measurements, rate of primary photosynthetic production is calculated by appropriately programmed computer means. Readout means are provided to indicate the rate of primary production. Further, concentrations of chlorophyll that generate the primary production are also determined by means of the apparatus of this invention. The method of this invention, employing measurement instruments of the type disclosed, enables the determination of concentrations of chlorophyll and primary production in parcels of water.

54 Claims, 5 Drawing Sheets

METHOD AND APPARATUS FOR DETERMINING CONCENTRATIONS OF CHLOROPHYLL AND THE RATE OF PRIMARY PRODUCTION IN WATER

FIELD OF THE INVENTION

The invention relates generally to an instrument having means for sensing irradiance to determine the input of photosynthetic energy to a parcel of water, a detector to measure fluorescence per unit volume of water and appropriate circuitry and calculation means to determine concentrations of chlorophyll and rates of primary photosynthetic production.

BACKGROUND OF THE INVENTION

The measurement of primary photosynthetic production in natural waters is of fundamental importance in ecological studies. Despite significant advances in the application of optical methods to biological oceanography, until now direct measures of primary production have been expensive, time consuming and subject to controversy. Primary production measurement by incubation of water samples inoculated with appropriate substances provides questionable results, due in part by the poor simulation of ambient light and temperature fields as they actually occur in nature.

Some of the reasons why it is important to develop inexpensive sensors for measurement of chlorophyll concentrations and primary production include the monitoring of global productivity, measuring global fisheries resources, application of above surface to underwater optical communication systems, underwater detection applications and correlation and calibration of remote sensing systems. While attempts have been made to determine primary productivity, they have been very man-power and cost intensive. The measurement of primary production is one of the most important activities of oceanographers at sea but, until now, it has been one of the most time-consuming and inaccurate of measurements. The accurate, rapid and economical measurement of primary production would aid in rapid expansion of understanding of spatial and temporal variability in production.

Measurement of light in natural waters has been conducted for many years. Recently, measurements of spectral irradiance in the ocean have indicated certain anomalies in the spectral region of 660 to 700nm (nanometers), which is the region of chlorophyll fluorescence. These anomalies have been higher than predicted when considering measurements of irradiance in this spectral region. This phenomenon has been noted but little exploited until recently. This may have been due to the specialized instruments required to accurately measure chlorophyll fluorescence in the presence of a highly variable background signal and by disagreement on its origin. One researcher first attributed the phenomenon to anomalous dispersion. A further complication to its interpretation is its dependence on a highly variable underwater light field and the complex set of factors influencing fluorescence yield.

Researchers had concentrated their measurements to the attenuation in water, according to Beers law, of the surface irradiance. Such measurements usually included the entire spectrum (400-700nm) of photosynthetically active radiation. This led first to estimates of chlorophyll concentration based on the attenuation of light by chlorophyll absorption. From these measurements of the absorption coefficient at different wavelengths, estimates based upon empirical models were made regarding primary production. Evidence of fluorescence excited by sunlight was occasionally detected but deemed to be anomalous and was ignored.

The contribution of fluorescence to upwelling irradiance in waters has been analyzed. One researcher considered Raman scattering as a possible source and rejected it. Other researchers calculated fluorescence efficiencies and chlorophyll concentrations from their measurements. It does not appear that any of them related their measurements to primary production. Before the present invention, researchers in this area did not think it possible to construct an instrument from which primary production could be determined from sensing the level of fluorescence.

Part of the problem faced by researchers in determining primary production in a parcel of water is that many pigments with different absorption spectral characteristics can couple energy to chlorophyll and on to photosynthesis. Furthermore, this mix of pigments is highly variable in nature. This can cause production estimates based on chlorophyll concentration to often give poor results. In addition, optical remote sensing methods based on light attenuation or on reflectance cannot discriminate between living organisms and non-living detritus.

Furthermore, estimates of primary production based on measurements of chlorophyll, such as those obtained from instruments with artificial excitation light sources tuned to chlorophyll, while usually giving reasonable estimates of chlorophyll, do not account for the input of photosynthetic energy through other pigment systems.

SUMMARY OF THE INVENTION

Recognition that measurements of chlorophyll a fluorescence enable determination not only of concentration of chlorophyll, but of primary production, is a significant factor in this invention. In accordance with this invention, by measuring the naturally occurring radiance at the wavelength of chlorophyll fluorescence, it was found that the chlorophyll concentration causing this radiance could be calculated. Even more importantly, by considering the biophysical source of this fluorescence and a knowledge of these mechanisms in photosynthetic organisms, it was found that primary production could be measured. The invention comprises a unique combination of optical sensors and electronic circuitry that permits the sensing of naturally occurring fluorescence from plant pigments, in this case, chlorophyll a. By making this measurement, along with the measurement of the energy exciting this natural fluorescence, it is possible to calculate concentrations of chlorophyll and rate of primary photosynthetic production in predetermined parcels of water in lakes and oceans.

It is therefore an important object of this invention to combine in one instrument two different types of optical sensors, along with appropriate electronics, into an underwater instrument suitable for making the appropriate measurements mentioned above. Together with the underwater sensor package, appropriate data acquisition and processing or calculation components may be used to present the user with instantaneous readings of chlorophyll a concentrations and rates of primary productivity.

The invention can be divided into constituent parts. First, the fluorescent excitation energy (normally from the sun) or irradiance is measured, preferably by means of a scalar detector. In the specific embodiment for the measurement of chlorophyll fluorescence and primary production, excitation energy is photosynthetically active radiation (PAR), typically measuring all radiation between 400 and 700nm incident upon an underwater point from all directions. Secondly, a detector of the type known as a Gershun tube is employed as a radiance detector. This detector preferably has a narrow bandwidth, typically 10nm, centered at the wavelength of maximum emission, in this case, 683nm for chlorophyll a. This radiance detector is arranged so that it views a portion of water away from the excitation source (normally the sun) referred to as the upwelling light field. This arrangement permits use of the instrument in surface waters either without the interference of sunlight or it minimizes the interference of sunlight.

An alternative would be to measure upwelling irradiance with a narrow bandwidth detector. A second alternative is to measure a spherical section of radiance, typically a 10° wide band of radiance, about the "waist" of the instrument package. This design would have the advantage of viewing a portion of water out of the "shadow" of the instrument.

A third aspect of the invention is the integration of the two types of optical sensors into one instrument with appropriate electronics and computational methods and apparatus for the determination of concentration of chlorophyll and rates of primary production.

In another alternative embodiment, the system includes means for measuring the light incident upon the water surface, in addition to measuring the underwater irradiance at the location desired and measuring the generated fluorescence. This embodiment also includes means of measuring the depth below the surface of the water where the sensor assembly is located, and means for coupling all of these signals into the appropriate computer and calculating the result which is, primarily, the rate of primary production.

BRIEF DESCRIPTION OF THE DRAWING

The objects, advantages and features of this invention will be more readily perceived from the following detailed description when read in conjunction with the accompanying drawing, in which.

DESCRIPTION OF THE PREFERRED EMBODIMENT

Figure 1:
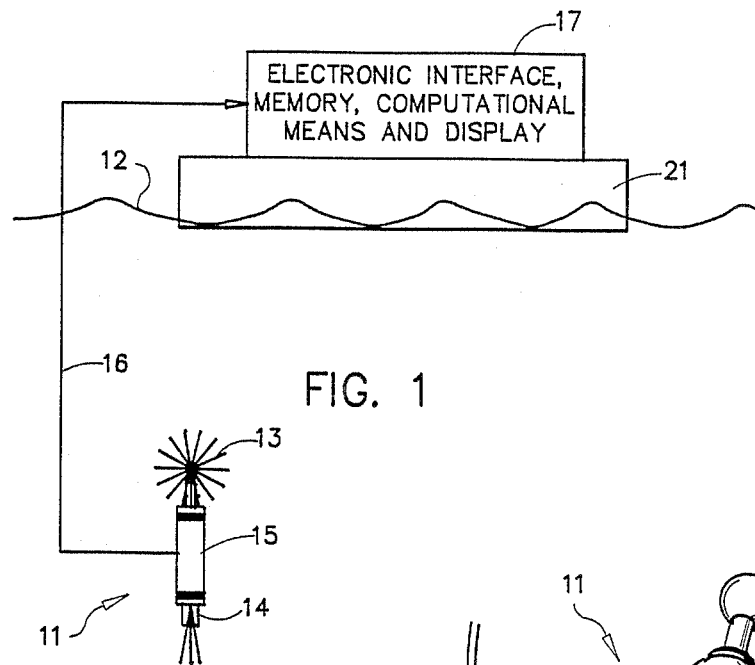
FIG. 1 is a schematic representation of the instrument of the invention positioned underwater and coupled to electronic apparatus on a floating platform.

In order to fully understand the invention and its purposes and functions, it is appropriate to review the optical theory with an orientation toward determining concentration of chlorophyll and rates of primary production in a parcel of water. The first step in the measurement of chlorophyll and primary production is the determination of the amount of light available for absorption into photosynthetic pathways. This quantum flux of absorbed light can be measured in several ways. Commonly, photosynthetically active radiation (PAR), defined to be the total quantum flux between 400 and 700nm, is measured. The detector often used is a cosine collector that measures vector irradiance. The preferred detector is spherical and measures scalar irradiance, providing a more accurate reading of available excitation energy. A cosine detector could be used with an appropriate factor to account for the difference between geometric and optical path length and for the fact that the light field in the ocean is partially diffuse.

The detection of cellular fluorescence in natural waters is governed principally by two major environmental factors. One is the absorption of the fluoresced flux by the water between the excited cell and the detector. The other major environmental factor is the direct and scattered light from the sun. Water at the wavelength of chlorophyll fluorescence (683nm) has an attenuation coefficient approximately 25 times that of the blue (435nm). The importance of this fact is not immediately evident until it is realized that chlorophyll a is most highly stimulated by irradiance at 435nm, which is attenuated relatively much less than light of other wavelengths. Given the fact that 683nm fluorescence is highly attenuated in water, substantially any measurable 683nm light below the water surface must be a result of chlorophyll fluorescence. For this same reason, the volume of water containing photosynthetically active material is relatively close to the radiance detector, normally less than five meters. Consequently, the variation in the attenuation coefficient at 683nm is relatively unaffected by the variations in the concentrations of the particulate and dissolved materials in the water.

The determination of the rates of primary production is derived through the relationship of the partition of energy in basic photosynthetic systems. For all practical purposes, when the quantum of energy is absorbed into the photosynthetic apparatus, the energy is dissipated by one of three methods: (1) fluorescence; (2) photosynthetic fixation of carbon, or primary production; or (3) by thermal loss. Recent biophysical studies have suggested that this partitioning is predictable, the ratios between the three being substantially constant. Thus, by measuring the fluorescent emission of chlorophyll or other synthetic pigment of a parcel of water, the rate of primary production can be determined. On the other hand, the rate the carbon fixation occurs (primary production) depends on the input energy and the organisms available. Thus, by knowing the irradiance and the produced radiance it is possible to estimate the productive capacity of the system under other input energy levels. Another important point is that by measuring upwelling radiance, chlorophyll concentration can be determined when the value of irradiance is combined with the radiance value.

The various general tools and equations which enable one to determine the concentration of chlorophyll and the rate of primary production in a parcel of water will be described below together with the apparatus and methods.

Chlorophyll is not the only organism component of potential interest. The in vivo fluorescence measurements of photosynthetic pigments such as that of chlorophyll a, phycoerythrin and phycocyanin leads to estimates of pigment concentration, phytoplankton and cyanobacterial crop size, but most importantly, to primary production.

With reference now to the drawing, and more particularly to FIG. 1, there is shown in schematic form detecting instrument 11 positioned beneath surface 12 of the water in which it is submerged. The instrument has a scalar irradiance detector 13 pointing upwardly to detect PAR and detector 14 pointing downwardly to detect upwelling radiance. Simple electronic circuitry comprising amplifiers to condition the signals from the photodetectors are contained in main body 15 of the instrument. By means of wire 16 the signals from the circuitry in main body 15 are conducted to block 17 on floating platform 21. Block 17 contains the remaining portion of the system, typically comprising electronic interface, memory, computational and display means.

Figure 2:
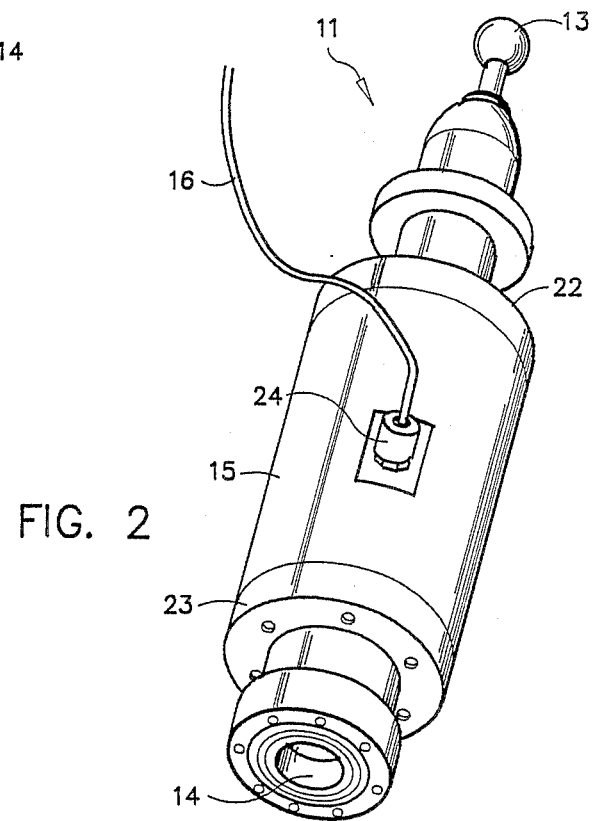
FIG. 2 is an enlarged perspective view of a preferred embodiment of the detector instrument of FIG. 1.

FIG. 2 is an enlarged view of a practical embodiment of instrument 11 of FIG. 1. Main body 15 is the portion of the instrument between coupling collars 22 and 23. Sensor 13 and its accompanying optics is that portion of the instrument above collar 22 while detector 14 is located within and below that portion of the instrument including collar 23.

In general terms, detector 14 is the radiance detector and is comprised of a photodetector, appropriate optical filters to give the detector a narrow bandwidth at the desired wavelength of maximum fluorescence, appropriate internal baffles to limit the acceptance angle of the entering light to a narrow field of view and a window through which light passes and which keeps water out. This has been referred to as a Gershun tube.

A portion of the instrument including detector 13 is a preferred optical collector for measuring scalar irradiance and is composed of a collecting sphere designed to select photons from all directions, a series of filters and internal optics to transmit the light from the sphere to a photodetector, and appropriate housing means to make the sensor water tight. Main body 15 of instrument 11 contains the electronics for amplification and processing of signals from the photodetectors. Connector means 24 is provided for connecting an electrical cable to appropriate readout means or data acquisition means located remotely. In this case, that would be the equipment located in block 17 of FIG. 1.

Figure 3:
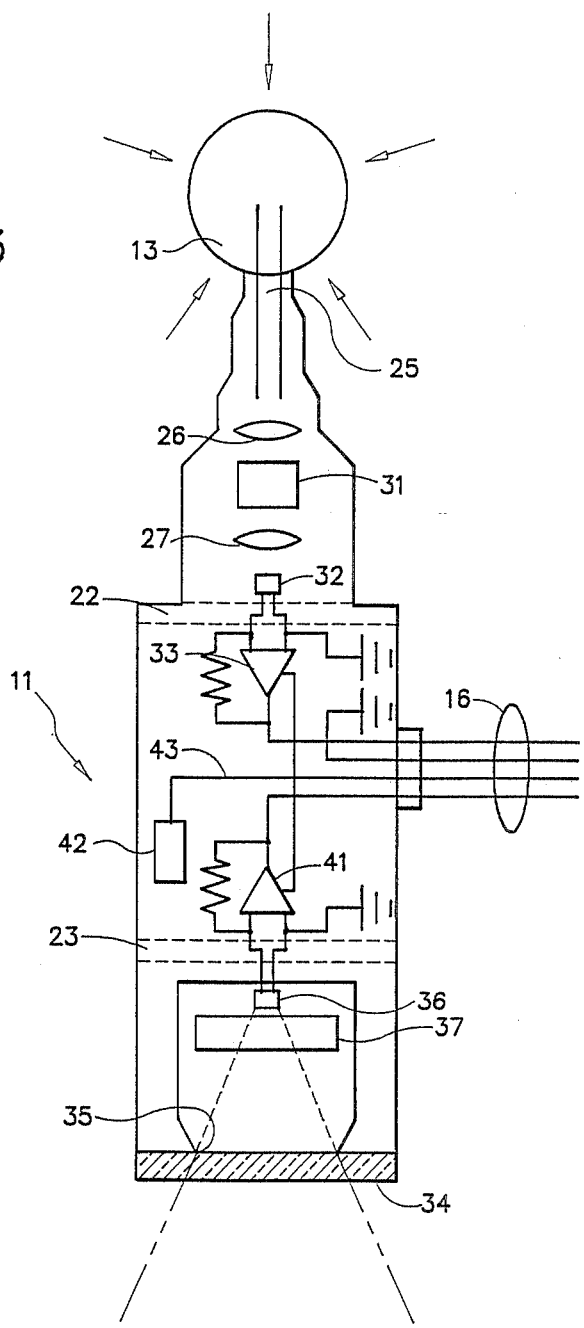
FIG. 3 is a schematic view of the optics and electronic circuitry in the instrument of FIG. 2.

FIG. 3 is a somewhat more detailed view of the arrangement of the radiance (fluorescent emission) and scalar irradiance (fluorescent excitation) detectors, along with a very simple form of the necessary circuitry needed to produce a voltage that can be sent to the data recording, computation and display means. It is possible that more of the circuitry could be located in the underwater instrument, including recording means to record the detector signals for later processing after the instrument has been retrieved from the water.

Instrument 11 shown in FIG. 3 is placed in an underwater light field by lowering it from a ship or other suitable floating platform. The instrument may be held in an appropriate frame so that sphere 13, which is preferably made from suitable material such as polytetrafluoroethylene, is pointed upward toward the surface. Light from various directions is incident on this sphere, is diffused inwardly and enters a light pipe or fiber optic 25 made from material such as a solid quartz rod. The light is conducted through the fiber optic toward lenses 26, 27 in the interior of the housing. This would be in that portion between collar 22 and sphere 13. Filter assembly 31 is provided to shape the resulting spectral response of the combination of ball, light pipe and photodetector, to resemble the fluorescent excitation spectrum of the pigment of interest, normally chlorophyll. Photodetector 32 is normally a silicon photodiode, such as a UV100B made by EG&G, Inc. Current from the photodetector flows into amplifier 33, such as a LM11 made by National Semiconductor Corporation, configured to operate as a current-to-voltage converter. This amplifier produces an output voltage that is proportional to the input fluorescent excitation energy. This voltage is sent by means of the cable, indicated collectively by reference numeral 16, to the surface where it is recorded or displayed or both, by means of the system components previously mentioned. As stated above, the amplifier output signal could be recorded internally and later played back for further processing.

Simultaneously with the detection of the fluorescent excitation energy as described above, fluorescent emission is typically detected with the radiance detector located at the opposite end of the instrument. Optically clear window 34 transmits light from the water volume that the instrument is viewing. The field of view of the instrument is determined by field stop 35 located directly behind window 34, and by the size of photodetector 36. Detector 36 is also normally a silicon photodiode but other types of detectors, such as photomultipliers, may be used. Filter assembly 37 normally comprises an interference filter and suitable glass blocking filters. Filtered fluorescent emission incident on photodetector 36 creates a current that flows to amplifier 41 which is also configured as a current-to-voltage converter. The voltage from amplifier 41 is then sent via cable 16 to the surface where it is recorded or displayed or both. Again, the signal from amplifier 41 can be recorded internally and employed later.

Typically, the components and apparatus between window 34 and sphere 13 are contained within a waterproof housing fabricated from aluminum or other appropriate material and provided with suitable O-ring seals as appropriate. It is unnecessary to provide detailed description of this conventional structure. Amplifiers 33 and 41 are provided with appropriate electrical power by power conditioner 42. This power may be supplied with appropriate voltage from a power source at the surface and received over cable 16 by means of wire 43, or it may be provided by a local battery or other power supply located within the instrument housing.

Figure 5:
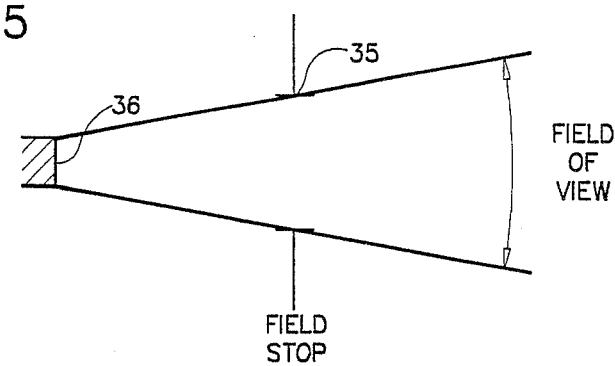
FIG. 5 is a schematic representation of the structure defining the field of view of a Gershun tube.

The basic optics of the Gershun tube are shown in FIG. 5. It is a very simple optical detector with a field of view limited by the combination of the diameter of detector 36 and the diameter of field stop 35.

Figure 6:
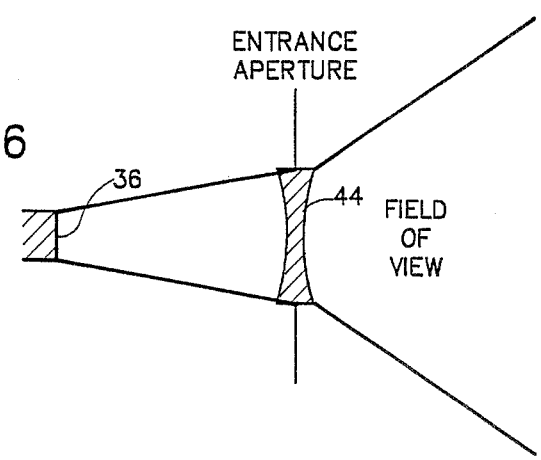
FIG. 6 is a schematic representation of a radiance telescope, alternative to a Gershun tube.

The simple optics of a radiance telescope an alternative embodiment to the Gershun tube, modified for larger field of view, are shown in FIG. 6. Here the field of view is formed by a combination of lens 44 and the size of photodetector 36.

It is also possible that other forms of geometrical optics could be used in the fluorescent emission detector.

Figure 7:
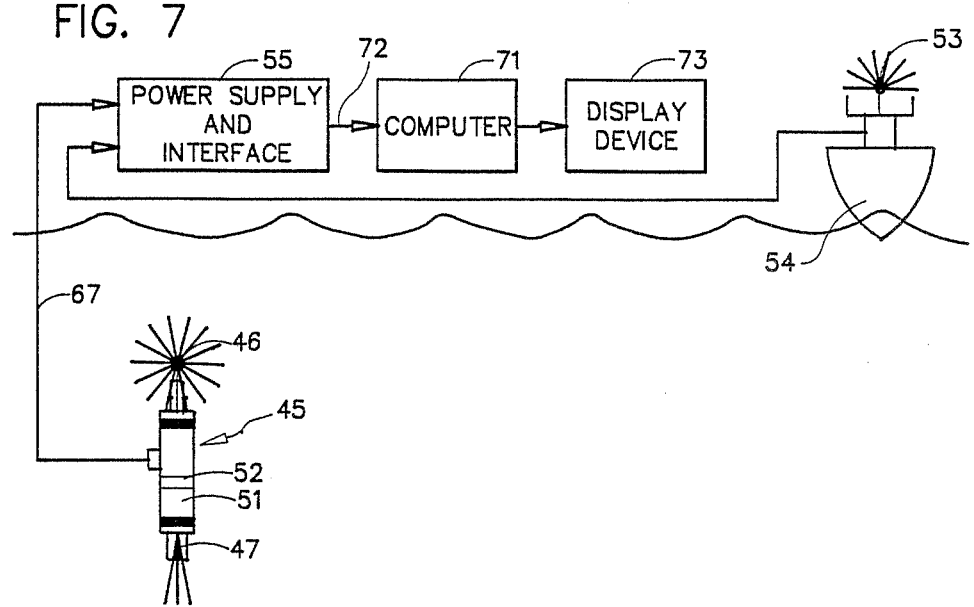
FIG. 7 is a schematic representation similar to FIG. 1, of an alternative instrument constructed in accordance with the invention.

An alternative embodiment of the system of the invention is shown in FIG. 7. The underwater instrument 45 is substantially the same as instrument 11 previously described. That is, it has scalar irradiance detector 46 and radiance detector 47 positioned at opposite ends. Main body section 51 is formed with a depth sensor 52, the signals from which will be discussed below. Another sensor is also used in this embodiment, that being sensor 53 measuring the light incident upon the water surface. Sensor 53 is located on the top of the measuring platform, which is typically a boat or ship 54. Sensor 53 measures the scalar irradiance from the sun and sky over the wavelength region known to be usable for primary production, namely, 400 to 700nm. The resulting voltage signal from this sensor is transmitted to a digitizer located in power supply and interface unit 55.

The sunlight enters the water surface and is attenuated by the water and its constituents as it passes downward. The underwater sensor assembly utilizes sensor 46 for measuring scalar irradiance as previously described. The signal from this sensor is processed as will be described presently. This sensor measures PAR, the amount of energy available to excite photosynthesis and thus primary production. This sensor also measures the rate of attenuation of light in the water column, a parameter that will be used in other calculations.

The depth measuring device is normally a pressure transducer 52. The organisms in the water at the depth measured by transducer 52 are excited by the sunlight at that depth as measured by sensor 46 and consequently fluoresce, causing light of a longer wavelength to be emitted in the water. Sensor 47 measures the radiance existing in the water at the wavelength of chlorophyll fluorescence, normally 683nm. The sensor and the associated filters have previously been described. The photodetector of sensor 47 normally views the volume of water in the downward direction to avoid being affected by direct sunlight. The field of view of this sensor has been discussed. The current from this sensor will also be described below.

Figure 8:
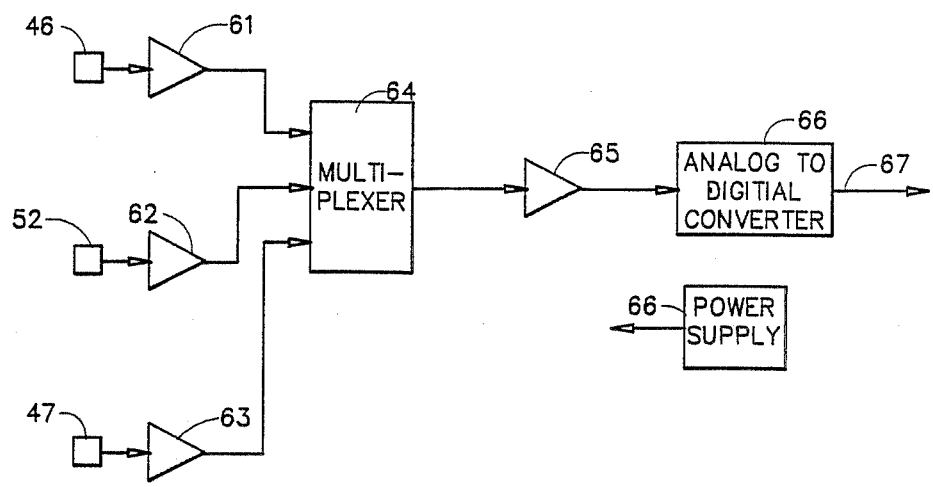
FIG. 8 is a schematic view of the electronic circuitry within the body of the instrument of FIG. 7.

With reference now to FIG. 8, the current output of scalar irradiance sensor 46 is amplified and converted to a voltage by a current-to-voltage converter amplifier 61. The output of amplifier 61 then goes to voltage multiplexer 64. The output of pressure transducer 52 is amplified by amplifier 62, the output of which is applied to the voltage multiplexer. Similarly, photodetector 47, normally operating in the photovoltaic mode, has its output applied to amplifier 63, functioning as a current-to-voltage converter. The output of amplifier 63 is also applied to multiplexer 64.

Multiplexer 64, to which the three signals from amplifiers 61, 62 and 63 are connected, enables the data acquisition system in the underwater housing to sequentially select each signal. As each signal is selected, it is typically amplified by amplifier 65 and digitized by analog to digital converter 66. The resulting digital data is transmitted to the surface by suitable means such as frequency-shift-keying or current loop serial. In either event, cable 67 connects the circuitry of FIG. 8 to the electronics shown in FIG. 7 situated above water.

For each location, a series of readings are taken at different depths from a point just below the surface to as much as 200 meters. This data is recorded in memory for use by the computer in computing the outputs described below, and is referred to as a vertical profile.

Surface sensor 53 on the floating platform, such as ship 54, provides a signal which is digitized and combined with the signals from the underwater sensor system. This digitized combined signal is transmitted to computer 71, typically by means of an RS-232C bus 72. Display device 73 may be any appropriate type, such as digital or pictorial such as a CRT. It may be made to display measurements from instrument 45 or computed data from the computer.

The digitized signals from the sensors described above are then available for analysis by a suitable computer program operating during creation of the vertical profile. To determine the rate of primary production the computer program will apply appropriate calibration constants for the sensors and apply suitable equations. This will be discussed in conjunction with FIG. 4.

An example of this process would be to first calculate the radiance at 683nm by applying the following equation:

$$Lu(683) = C_R(V_R - V_{Ro}) \qquad (1)$$

where $Lu(683)$ is the radiance at 683nm, $V_R$ is the voltage from sensor 47 representing detected radiance, $V_{Ro}$ is the dark or 0 voltage from sensor 47 and $C_R$ is the calibration constant for sensor 47 that relates the voltage signal to the measured radiance.

In a similar fashion the scalar irradiance is calculated by the following equation:

$$E_o = C_I(V_I - V_{Io}) \qquad (2)$$

where $E_o$ is the scalar irradiance (PAR), $V_I$ is the sensor voltage, $V_{Io}$ is the dark voltage and $C_I$ is the calibration constant for sensor 46.

The fluorescence per unit volume of water (F) is calculated from the radiance signal by the following equation:

$$F = \frac{4\pi K(683) Lu(683)}{D_w} \qquad (3)$$

where $K(683)$ is the attenuation coefficient describing the rate of attenuation of diffuse radiance at 683nm and $D_w$ is the detector function which specifies the ratios of the emission spectra of chlorophyll to the detector response function. It, in effect, relates detector bandwidth and fluorescence bandwidth. A typical value for $D_w$ is 0.037 for a three-cavity interference filter for peak transmission at 683nm.

The primary production of photosynthesis per unit volume $P_p$ is calculated from the following relationship:

$$P_p = \frac{FQ_p}{Q_f} \qquad (4)$$

where $Q_p$ is the quantum efficiency of production and $Q_f$ is the quantum efficiency for fluorescence. $Q_p$ and $Q_f$ are functions of scalar irradiance $E_o$. Both $Q_p$ and $Q_f$ are constants in the first order and are modified by detected irradiance $E_o$ for second order corrections for very high and very low levels of excitation energy. Below a threshold light level, even with some detectable irradiance, there may be measurable fluorescence but no photosynthetic production. Similarly, at very high excitation energy levels, production resulting therefrom ceases to be linear and levels off significantly. When the irradiance value $E_o$ is applied to the equation for primary production, the high and low ends can be accounted for to ensure accurate readings for primary production.

The quanta of energy absorbed per unit volume of water per unit chlorophyll concentration is calculated in block 81 (FIG. 4) from the relationship $$F_{ao} = E_o(1 - e^{-a}) \quad (5)$$

where a is the absorption coefficient per unit pigment concentration. Note that the irradiance value $E_o$ is the variable in determining $F_{ao}$.

An additional benefit of this system is the ability to calculate the concentration of the pigment chlorophyll in algae in the water. Having obtained measures for Eo and Lu(683) at a given depth, the following equation can be used to calculate concentration of chlorophyll (C) at the depth of the sensors:

$$C = \frac{4\pi K(683) Lu(683)}{F_{ao} \phi D_w} \quad (6)$$

where $\phi$ is the fluorescence efficiency of chlorophyll, a constant.

The relationship between the quantum efficiencies of production and fluorescence is known to be affected by the ambient light levels, in addition to other secondary effects. To improve the accuracy of the prediction of primary production, models based on ambient light levels as measured by the scalar irradiance sensor may be applied to improve the prediction.

The above procedure assumes that the attenuation coefficient K(683) for radiance at 683nm is constant. The value for this coefficient will vary over a relatively narrow range and its value can be predicted from the attenuation coefficient of Eo which can be directly measured from the vertical profile that is recorded as described above. This attenuation coefficient ($K_{eo}$) can be calculated as follows:

$$K_{eo} = -\frac{1}{(Z_2 - Z_1)} \ln\left(\frac{E_{o2}}{E_{o1}}\right) \quad (7)$$

where $Z_1$ and $Z_2$ are two depths and $E_{o1}$ and $E_{o2}$ are the scalar irradiances at these two depths. In normal operation a "look-up" table, compiled from empirical data, would be used to apply a corrected value of K(683) from the calculated $K_{eo}$ and measured depth.

The incident scalar irradiance above the water surface E(O), measured as described above, can be used to estimate the potential for primary production. For example, if the measurement occurs during conditions of cloudiness, a lower rate of primary production will be expected to occur due to the reduced levels of excited radiation. Light levels for a cloud-free day can be relatively accurately predicted given a knowledge of sun angle. If measurements of primary production are obtained under less than ideal sky conditions, the measures of E(O) can, in conjunction with other empirical data, predict production under other sky conditions.

Figure 4:
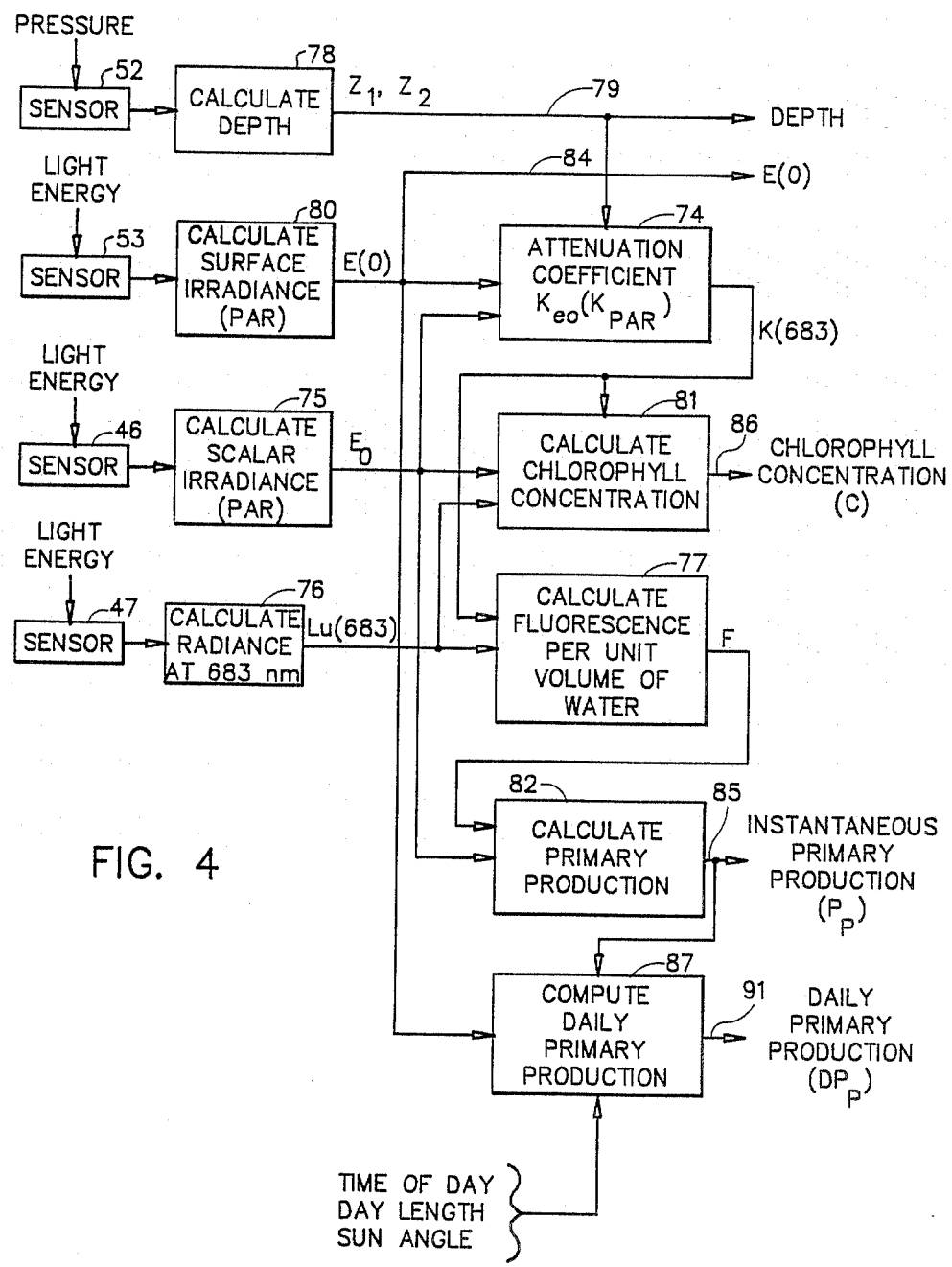
FIG. 4 is a block diagram of the processing apparatus for the signals from the circuitry of FIG. 3, also including the additional input signal from FIG. 7.

The above equations will now be related to the block diagram of FIG. 4. Pressure transducer 52 provides an electrical signal to block 78 which calculates the depth at which the transducer resides at that moment. A signal representing that depth is the output on line 79, shown as "$Z_1$, $Z_2$." Scalar irradiance above the surface of the water is detected by sensor 53 and an electrical signal E(O) representative of photosynthetically active radiation (PAR) is calculated and produced by block 80. Depth sensitive (input from line 79) attenuation coefficient $K_{eo}$ of Eq. (7) is applied to the E(O) signal in block 74, resulting in a corrected K(683) attenuation coefficient. The PAR signal E(O) is provided as an output on line 84.

The excitation energy applied to a parcel of water beneath the surface is detected by sensor 46 which causes an electrical signal to be applied to block 75 where scalar irradiance (PAR) is calculated through use of Eq. (2). The upwelling radiance is detected by sensor 47, resulting in an electrical signal applied to block 76 which calculates radiance [Lu(683)] according to Eq. (1). The radiance representing signal from block 76 is then applied to block 77 where fluorescence per unit volume of water (F) is calculated using Eq. (3). Block 82, with inputs F from block 77 and $E_o$ from block 75, calculates instantaneous rate of primary production as an output on line 85, employing Eq. (4).

Block 81 combines inputs $E_o$ from block 75 and Lu(683) from block 76, employing Eq. (5), to produce chlorophyll concentration output on line 86. To compensate for depth and turbidity, block 81 may also employ the attenuation coefficient K(683) from block 74. Note that in many instances, K(683) may be taken as a constant and would not require modification through block 74 to produce useful results.

The outputs of depth, surface irradiance, chlorophyll concentration and primary production are typically recorded and stored for later analysis or use. The value of these data increase as more data from the same and different water locations are accumulated, analyzed and categorized for use by oceanographers, the fishing industry and others.

Note that C is a quantity, the chlorophyll concentration, while $P_p$ is the rate at which chlorophyll a transforms sunlight into fixed carbon and oxygen.

The FIG. 4 block diagram covers the more complete system of FIG. 7, providing second order corrections for depth turbidity and non-linearity. These inputs come from sensor 52 for depth and sensor 53 for surface irradiance, with modifications due to actual irradiance detected by sensor 46. These corrections from depth (z) and actual irradiance ($E_o$) are applied to block 74 to calculate the attenuation coefficient $K_{eo}$ with an adjustment for measured depth.

The system of FIGS. 1-3 provides useful outputs of primary production and chlorophyll concentration without the surface irradiance and depth inputs. The system as thus described would include that portion of the FIG. 4 block diagram comprising sensors 46 and 47, and blocks 75, 76, 77, 81 and 82, applying Eqs. (1-6).

The most important information provided by the method and apparatus of this invention is primary production $P_p$. A raw, uncompensated value for $P_p$, which is nevertheless valuable, could be obtained by sensor 47 outputs, the radiance Lu(683) calculation of block 76, the unit fluorescence calculation F, using K(683) as a constant for the particular water parcel location, and the calculation of primary production $P_p$ in block 82. This basic system uses Eq. (1), (3) and (4) without second order corrections.

Instantaneous primary production as an output from block 82 is useful and may be employed in many ways. However, that output, integrated over a periood of 24 hours or several 24-hour periods, directly provides more useful information. This can be done by the computer in block 17 of FIG. 1. Additionally, with reference to FIG. 4, block 87 provides the integration function to produce daily primary production $DP_p$ on output line 91. That information can be recorded within the submerged instrument for later readout. From the recorded data a computer could trace a graph of production over a 24-hour period.

With reference again to the entire diagram of FIG. 4, block 87 combines input $P_p$ with surface irradiance E(O) and manual inputs of time of day, day length and sun angle to provide an estimate of $DP_p$ at any time from the instantaneous input signals. Thus by adding and relating input energy $E_o$ to $P_p$ rate, a daily or time production can be calculated. Then by relating the radiance $L_u(683)$ to the measured irradiance $E_o$ it is possible to calculate the chlorophyll a necessary to result in that amount of fluorescence at that input energy.

State another way, the basic output $P_p$ of block 82 is instantaneous rate of production. In order to obtain at least a good estimate of daily production, several readings of $P_p$ must be taken or irradiance must be added.

Then to get back to the complete system of FIG, 4, it is important to know the clarity or the turbulence of the water so that surface irradiance E(O) can be related to below surface irradiance $E_o$, the result being applied to upwelling radiance measurements.

Figure 9:
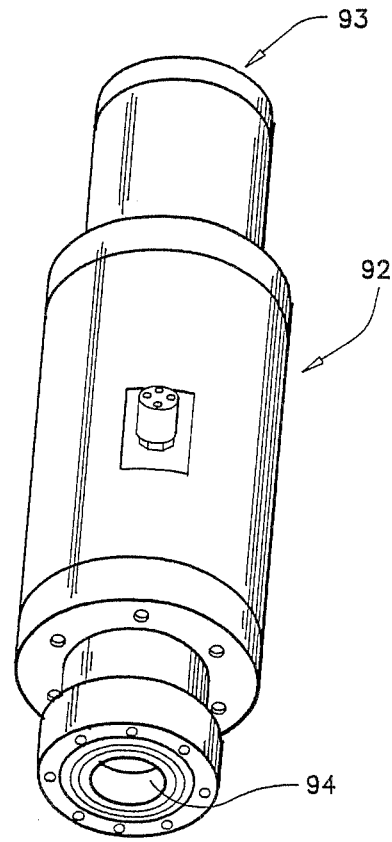
FIG. 9 is a perspective view similar to FIG. 2 of an alternative embodiment of the underwater sensing instrument of the invention.

The alternative embodiment of instrument 92, as shown in FIG. 9, employs a vector or cosine irradiance sensor 93 in place of the scalar sensor of FIG. 2. Radiance sensor 94 is one of the types described above. The basic difference is the equation needed to convert the output of the vector sensor to a value equivalent to that of a scalar sensor. This is merely a matter of mathematics and is not directly a part of this invention.

An alternative display presentation would be to produce a graphic plot of the parameters discussed above as a function depth. This could be a visual presentation of the vertical profile.

The above description has concentrated on the photosynthetic radiance of chlorophyll a, normally having a wavelength centered at 683nm. It is important to not that other pigments at other wavelengths may also be important in primary production at any given location. For example, phycoerythrin has a fluorescent emission centered at about 580nm, pursuant to peak excitation at about 500nm (instead of the 435nm for chlorophyll a). The excitation spectrum of 400–700nm holds true for all plants.

For these reasons, two or more detectors 47 may be needed for the different emission wavelengths. These could be structured as separate instruments 11 or individually tuned sensors could be located side-by-side behind the same window.

In view of the above description, it is likely that modifications and improvements which are within the scope of the appended claims will occur to those skilled in the art.

What is claimed is:

1. A method for determining the natural rate of photosynthetic primary production driven by natural light in a predetermined parcel of water, said method comprising the steps of:

sensing excitation energy resulting from naturally occurring radiant flux density applied by natural light to the predetermined parcel of water and existing in the parcel of water over a period of time;

producing an electrical signal representative of the sensed naturally occurring excitation energy;

sensing the naturally occurring fluorescent emission from within the predetermined parcel of water which emission exists in the parcel of water over a period of time as a result of the existing naturally occurring applied excitation energy;

producing an electrical signal representative of the sensed fluorescent emission;

combining the electrical signals representative of sensed naturally occurring excitation energy and sensed fluorescent emission; and calculating the rate of primary production in the predetermined parcel of water from said electrical signals.

2. The method recited in claim 1, and comprising the further steps of:

calculating fluorescence per unit volume of water from said step of producing a signal representative of sensed fluorescent emission;

producing an electrical signal representative of the calculated fluorescence per unit volume; and combining the electrical signals representative of sensed naturally occurring excitation energy and fluorescence per unit volume;

said primary production calculating step being the result of combining said signals representative of sensed excitation energy and fluorescence per unit volume.

3. The method recited in claim 2, and comprising the further step of computing daily primary production by integrating the rate of primary production over the period of at least one day.

4. The method recited in claim 2, and comprising the further steps of:

sensing excitation energy applied to the surface of the water;

producing an electrical signal representative of the sensed surface excitation energy;

producing a signal representative of instantaneous rate of primary productioon in the predetermined parcel of water;

combining the electrical signals representative of surface excitation energy and instantaneous rate of primary production with data as to time of day, day length and sun angle; and computing daily primary production from the signal combination including surface excitation energy.

5. The method recited in claim 4, and comprising the further steps of:

calculating the attenuation coefficient of the parcel of water;

producing an electrical signal representative of the attenuation coefficient; and applying the attenuation coefficient signal to said fluorescence per unit volume calculating step.

6. The method recited in claim 5, and comprising the further steps of:

sensing the pressure in the parcel of water;
calculating the depth of the parcel of water;
producing a signal representative of said depth and;

applying said depth signal to said attenuation coefficient calculating step to thereby further refine said attenuation coefficient.

7. The method recited in claim 5, wherein said attenuation coefficient is calculated from a combination of the signals representative of surface excitation energy and the sensed excitation energy.

8. A method for determining chlorophyll concentration in a predetermined parcel of water, said method comprising the steps of:
passively sensing fluorescent excitation energy resulting from naturally occurring radiant flux density applied by natural light to the predetermined parcel of water and existing in the parcel of water over a period of time;
producing an electrical signal representative of the sensed naturally occurring excitation energy;
sensing the naturally occurring fluorescent emission from within the predetermined parcel of water which emission exists in the parcel of water over a period of time as a result of the existing naturally occurring applied excitation energy;
producing an electrical signal representative of the sensed fluorescent emission;
combining the electrical signals representative of sensed naturally occurring excitation energy and sensed fluorescent emission; and
calculating the concentration of chlorophyll in the predetermined parcel of water from said electrical signals 9. A method for for determining chlorophyll concentration in a predetermined parcel of water, said method comprising the steps of:
sensing naturally occurring excitation energy applied to the surface of the water over a period of time;
producing an electrical signal representative of the sensed surface excitation energy;
calculating the attenuation coefficient of the parcel of walter;
producing an electrical signal representative of the attenuation coefficient;
sensing the naturally occurring fluorescent emission from witlhin the predetermined parcel of water which emission exists in the parcel of water over a period of time as a result of the existing naturally occurring applied excitation energy;
producing an electrical signal representative of the sensed fluorescent emission;
combining the attenuation coefficient signal with the sensed surface excitation energy and sensed fluorescent emission signals; and
producing a signal representative of chlorophyll concentration in the parcel of water from said combination of three signals.

10. A method for determining and predicting rate of photosynthetic primary production driven by natural light in a predetermined parcel of water, said method comprising the steps of:
sensing excitation energy resulting from naturally occurring radiant flux density applied by natural light to the predetermined parcel of water and existing in the parcel of water over a period of time;
producing an electrical signal representative of the sensed excitation energy;
sensing the naturally occurring fluorescent emission from within the predetermined parcel of water which emission exists in the parcel of water over a period of time as a result of the existing naturally occurring applied excitation energy;
producing an electrical signal representative of the sensed fluorescent emission;
sensing irradiance energy level above the surface of the water in which the predetermined parcel resides;
producing an electrical signal to correct for other levels of surface irradiance energy representative of the sensed surface irradiance energy;
combining the electrical signals representative of sensed excitation energy and sensed fluorescent emission;
calculating the rate of primary production in the predetermined parcel of water from said two combined electrical signals;
further applying the other level of surface irradiance energy electrical signal to the calculated rate of primary production and calculating the predicted rate of primary production; and
providing an output electrical signal representative of calculated and predicted rate of primary production under other naturally occurring conditions of irradiance in the predetermined parcel of water.

11. The method recited in claim 10, and comprising the further steps of:
calculating fluorescence per unit volume of water from said step of producing a signal representative of sensed fluorescent emissions;
producing an electrical signal representative of the calculated fluorescence per unit volume; and
combining the electrical signals representative of sensed excitation energy and fluorescence per unit volume;
said primary production calculating step being the result of combining said signals representative of sensed excitation energy and fluorescence per unit volume.

12. The method recited in claim 11, and comprising the further step of computing daily primary production by integrating the rate of primary production over the period of at least one day.

13. The method recited in claim 11, and comprising the further steps of:
producing a signal representative of instantaneous rate of primary production in the predetermined parcel of water;
combining the electrical signals representative of surface irradiance energy and instantaneous rate of primary production with data as to time of day, day length and sun angle; and
computing daily primary production from the signal combination including surface irradiance energy.

14. The method recited in claim 13, and comprising the further steps of:
calculating the attenuation coefficient of the parcel of water;
producing an electrical signal representative of the attenuation coefficient; and
applying the attenuation coefficient signal to said fluorescence per unit volume calculating step.

15. The method recited in claim 14, and comprising the further steps of:
sensing the pressure in the parcel of water;
calculating the depth of the parcel of water;
producing a signal representative of said depth;

applying said depth signal to said attenuation coefficient calculating step to thereby further refine said attenuation coefficient.

16. The method recited in claim 14, wherein said attenuation coefficient is calculated from a combination of the signals representative of surface irradiance energy and the sensed fluorescent excitation energy.

17. A method for determining the natural rate of photosynthetic primary production driven by natural light in a predetermined parcel of water, said method comprising these steps of:
sensing the naturally occurring fluorescent emission from within the predetermined parcel of water which emission exists in the parcel of water over a period of time as a result of being driven by natural light;
producing an electrical signal representative of the sensed fluorescent emission;
calculating the rate of primary production in the predetermined parcel of water from said electrical signal; and
producing a signal representative of the instantaneous rate of primary production in the parcel of water.

18. The method recited in claim 17, and comprising the further step of computing daily primary production by integrating the rate of primary production over the period of at least one day.

19. The method recited in claim 17, and comprising the further steps of:
sensing the pressure in the parcel of water;
calculating the depth of the parcel of water;
producing a signal representative of said depth; and
applying said depth signal to the signal representative of instantaneous rate of primary production to thereby further refine said signal representative of instantaneous rate of primary production.

20. A method for determining the natural rate of photosynthetic primary production and chlorophyll concentration driven by natural light in a predetermined parcel of water, said method comprising the steps of:
sensing excitation energy resulting from naturally occurring radiant flux density applied by natural light to the predetermined parcel of water and existing in the parcel of water over a period of time;
producing an electrical signal representative of the sensed naturally occurring excitation energy;
sensing the naturally occurring fluorescent emission from within the predetermined parcel of water which emission exists in the parcel of water over a period of time as a result of the existing naturally occurring applied excitation energy;
producing an electrical signal representative of the sensed fluorescent emission;
combining the electrical signals representative of sensed excitation energy and sensed fluorescent emission;
calculating the rate of primary production and concentration of chlorophyll in the predetermined parcel of water from said electrical signals; and
providing a first output electrical signal representative of calculated primary production in the predetermined parcel of water, and a second output electrical signal representative of calculated chlorophyll concentration in the predetermined parcel of water.

21. The method recited in claim 20, and comprising the further steps of:
calculating fluorescence per unit volume of water from said step of producing a signal representative of sensed fluorescent emission;
producing an electrical signal representative of the calculated fluorescence per unit volume; and
combining the electrical signals representative of the sensed excitation energy and fluorescence per unit volume;
said primary production calculating step being the result of combining said signals representative of sensed excitation energy and fluorescence per unit volume.

22. The method recited in claim 21, and comprising the further step of computing daily primary production by integrating the rate of primary production over the period of at least one day.

23. The method recited in claim 21, and comprising the further steps of:
sensing excitation energy applied to the surface of the water;
producing an electrical signal representative of the sensed surface excitation energy;
producing a signal representative of instantaneous rate of primary production in the predetermined parcel of water;
combining the electrical signals representative of surface excitation energy and instantaneous rate of primary production with data as to time of day, day length and sun angle; and
computing daily primary production from the signal combination including surface excitation energy.

24. The method recited in claim 23, and comprising the further steps of:
calculating the attenuation coefficient of the parcel of water;
producing an electrical signal representative of the attenuation coefficient; and
applying the attenuation coefficient signal to said fluorescence per unit volume calculating step.

25. The method recited in claim 24, and comprising the further steps of:
sensing the pressure in the parcel of water;
calculating the depth of the parcel of water;
producing a signal representative of said depth;
applying said depth signal to said attenuation coefficient calculating step to thereby further refine said attenuation coefficient.

26. The method recited in claim 25, and comprising the further steps of:
combining the attenuation coefficient signal with the sensed excitation energy and sensed fluorescent emission signals; and
producing a signal representative of chlorophyll concentration in the parcel of water from said combination of three signals.

27. The method recited in claim 24, wherein said attenuation coefficient is calculated from a combination of the signals representative of surface excitation energy and the sensed excitation energy.

28. Apparatus for determining the natural rate of photosynthetic primary production driven by natural light in a predetermined parcel of water, said apparatus comprising:
first detector means for sensing the naturally occurring excitation energy resulting from naturally occurring radiant flux density applied by natural light in the predetermined parcel of water and existing in the parcel of water over a period of time;

means connected to said first detector means for producing a first electrical signal representative of the detected naturally occurring excitation energy;

second detector means for sensing the naturally occurring fluorescent emission from within the water in the predetermined parcel of water which emission exists in the parcel of water over a period of time as a result of the existing naturally occurring applied excitation energy;

means connected to said second detector means for producing a second electrical signal representative of the detected fluorescent emission; and first computation means for combining said first and second electrical signals, said first computation means having an output providing a signal representative of the rate of primary production.

29. The apparatus recited in claim 28, and further comprising:

means connected to said second signal producing means for calculating fluorescence per unit volume of water and producing an electrical signal representative thereof, said signal being coupled to said computation means.

30. The apparatus recited in claim 29, and further comprising means connected to said output of said computation means for calculating daily primary production.

31. The apparatus recited in claim 30, wherein said daily primary production calculating means comprises integration means.

32. The apparatus recited in claim 30, and further comprising:

third detector means for sensing irradiance energy level above the surface of the water in which said predetermined parcel resides;

means connected to said third detector means for producing as an output a third electrical signal representative of said above surface irradiance energy level;

the output signal from said computation means representing instantaneous rate of primary production;

means combining said instantaneous rate output signal and said third signal and producing an output signal representing daily primary production.

33. The apparatus recited in claim 32, and further comprising:

means connected to the outputs of said third signal producing means and said first signal producing means to produce a signal representing the attenuation coefficient of the parcel of water;

said attenuation coefficient signal being connected to said fluorescence per unit volume calculating means to refine the output thereof.

34. The apparatus recited in claim 33, and further comprising:

fourth detector means for sensing pressure and producing an output signal indicative thereof;

means connected to said output of said fourth detector means for producing as an output a fourth electrical signal representative of depth of said fourth detector, said fourth electrical signal being connected to said attenuation coefficient signal producing means to enable said attenuation coefficient signal to be further refined.

35. The apparatus recited in claim 28, and further comprising:

second computation means for combining said first and second electrical signals, said second computation means having an output providing a signal representative of the concentration of chlorophyll in the parcel of water.

36. The apparatus recited in claim 28, and further comprising means for visually indicating the rate of primary production.

37. The apparatus recited in claim 28, and further comprising means for recording said first and second electrical signals for later operation thereon.

38. The apparatus recited in claim 28, and further comprising means for recording said signals representing the calculated rate of primary production.

39. Apparatus for determining the natural rate of photosynthetic primary production driven by natural light at a predetermined level in a body of water, said apparatus comprising:

detector means for sensing the naturally occurring fluorescent emission from within the water which emission exists at the predetermined level in the water over a period of time as a result of being driven by natural light;

means for producing an electrical signal representative of the detected fluorescent emission; and computation means for providing a signal representative of the rate of primary production from the electrical signal representative of the detected fluorescent emission.

40. A method for determining rate of primary production in a predetermined parcel of water, said method comprising the steps of:

sensing excitation energy applied to the predetermined parcel of water;

producing an electrical signal representative of the sensed excitation energy;

sensing fluorescent emission from within the predetermined parcel of water;

producing an electrical signal representative of the sensed fluorescent emission;

combining the electrical signals representative of sensed excitation energy and sensed fluorescent emission;

calculating the rate of primary production in the predetermined parcel of water from said electrical signals;

calculating fluorescence per unit volume of water from said step of producing a signal of sensed fluorescent emission;

producing an electrical signal representative of the calculated fluorescence per unit volume;

combining the electrical signals representative of sensed excitation energy and fluorescence per unit volume;

said primary production calculating step being the result of combining said signals representative of sensed excitation energy and fluorescence per unit volume;

sensing excitation energy applied to the surface of the water;

producing an electrical signal representative of the sensed surface excitation energy;

producing a signal representative of instantaneous rate of primary production in the predetermined parcel of water;

combining the electrical signals representative of surface excitation energy and instantaneous rate of primary production with data as to time of day, day length and sun angle; and computing daily primary production from the signal combination including surface excitation energy.

41. The method recited in claim 40, and comprising the further steps of:

calculating the attenuation coefficient of the parcel of water;

producing an electrical signal representative of the attenuation coefficient; and applying the attenuation coefficient signal to said fluorescence per unit volume calculating step.

42. The method recited in claim 41, and comprising the further steps of:

sensing the pressure in the parcel of water;

calculating the depth of the parcel of water;

producing a signal representative of said depth; and applying said depth signal to said attenuation coefficient calculating step to thereby further refine said attenuation coefficient.

43. The method recited in claim 41, wherein said attenuation coefficient is calculated from a combination of the signals representative of surface excitation energy and the sensed excitation energy.

44. A method for determining and predicting rate of primary production in a predetermined parcel of water, said method comprising the steps of:

sensing fluorescent excitation energy applied to the predetermined parcel of water;

producing an electrical signal representative of the sensed excitation energy;

sensing fluorescent emission from within the predetermined parcel of water;

producing an electrical signal representative of the sensed fluorescent emission;

sensing irradiance energy level above the surface of the water in which the predetermined parcel resides;

producing a corrective electrical signal representative of the sensed surface irradiance energy;

combining the electrical signals representative of sensed excitation energy and sensed fluorescent emission;

calculating the rate of primary production in the predetermined parcel of water from said two combined electrical signals;

further applying the corrective electrical signal to said two combined signals and calculating the predicted rate of primary production;

providing an output electrical signal representative of calculated and predicted rate of primary production in the predetermined parcel of water;

calculating fluorescence per unit volume of water from said sensed fluorescent emission producing step;

producing an electrical signal representative of the calculated fluorescence per unit volume;

combining the electrical signals representative of sensed excitation energy and fluorescence per unit volume;

said primary production calculating step being the result of combining said signals representative of sensed excitation energy and fluorescence per unit volume;

producing a signal representative of instantaneous rate of primary production in the predetermined parcel of water;

combining the electrical signals representative of surface irradiance energy and instantaneous rate of primary production with data as to time of day, day length and sun angle; and computing daily primary production from the signal combination including surface excitation energy.

45. The method recited in claim 44, and comprising the further steps of:

calculating the attenuation coefficient of the parcel of water;

producing an electrical signal representative of the attenuation coefficient; and applying the attenuation coefficient signal to said fluorescence per unit volume calculating step.

46. The method recited in claim 45, and comprising the further steps of:

sensing the pressure in the parcel of water;

calculating the depth of the parcel of water;

producing a signal representative of said depth; and applying said depth signal to said attenuation coefficient calculating step to thereby further refine said attenuation coefficient.

47. The method recited in claim 45, wherein said attenuation coefficient is calculated from a combination of the signals representative of surface irradiance energy and the sensed fluorescent excitation energy.

48. A method for determining rate of primary production and chlorophyll concentration in a predetermined parcel of water, said method comprising the steps of:

sensing excitation energy applied to the predetermined parcel of water;

producing an electrical signal representative of the sensed excitation energy;

sensing fluorescent emission from within the predetermined parcel of water;

producing an electrical signal representative of the sensed fluorescent emission;

combining the electrical signals representative of sensed excitation energy and sensed fluorescent emission;

calculating the rate of primary production and concentration of chlorophyll in the predetermined parcel of water from said electrical signals;

providing a first output electrical signal representative of calculated primary production in the predetermined parcel of water, and a second output electrical signal representative of calculated chlorophyll concentration in the predetermined parcel of water;

calculating fluorescence per unit volume of water from said sensed fluorescent emission producing step;

producing an electrical signal representative of the calculated fluorescence per unit volume;

combining the electrical signals representative of sensed excitation energy and fluorescence per unit volume;

said primary production calculating step being the result of combining said signals representative of sensed excitation energy and fluorescence per unit volume;

sensing excitation energy applied to the surface of the water;

producing an electrical signal representative of the sensed surface excitation energy;

producing a signal representative of instantaneous rate of primary production in the predetermined parcel of water;

combining the electrical signals representative of surface excitation energy and instantaneous rate of primary production with data as to time of day, day length and sun angle; and computing daily primary production from the signal combination including surface excitation energy.

49. The method recited in claim 48, and comprising the further steps of:

calculating the attenuation coefficient of the parcel of water;

producing an electrical signal representative of the attenuation coefficient; and applying the attenuation coefficient signal to said fluorescence per unit volume calculating step.

50. The method recited in claim 49, and comprising the further steps of:

sensing the pressure in the parcel of water;

calculating the depth of the parcel of water;

producing a signal representative of said depth; and applying said depth signal to said attenuation coefficient calculating step to thereby further refine said attenuation coefficient.

51. The method recited in claim 50, and comprising the further steps of:

combining the attenuation coefficient signal with the sensed excitation energy and sensed fluorescent emission signals; and producing a signal representative of chlorophyll concentration in the parcel of water from said combination of three signals.

52. The method recited in claim 49, wherein said attenuation coefficient is calculated from a combination of the signals representative of surface excitation energy and the sensed excitation energy.

53. Apparatus for determining rate of primary production in a predetermined parcel of water, said apparatus comprising:

first detector means for sensing the excitation energy applied in the predetermined parcel of water;

means connected to said first detector means for producing a first electrical signal representative of the detected excitation energy;

second detector means for sensing fluorescent emission from within the predetermined parcel of water;

means connected to said second detector means for producing a second electrical signal representative of the detected fluorescent emission;

first computation means for combining said first and second electrical signals, said first computation means having an output providing a signal representative of the rate of primary production;

means connected to said second signal producing means for calculating fluorescence per unit volume of water and producing an electrical signal representative thereof, said signal being coupled to said computation means;

means connected to said output of said computation means for calculating daily primary production;

third detector means for sensing irradiance energy level above the surface of the water in which said predetermined parcel resides;

means connected to said third detector means for producing as an output a third electrical signal representative of said above surface irradiance energy level;

the output signal from said computation means representing instantaneous rate of primary production;

means combining said instantaneous rate output signal and said third signal and producing an output signal representing daily primary production; and means connected to the outputs of said third signal producing means and said first signal producing means to produce a signal representing the attenuation coefficient of the parcel of water;

said attenuation coefficient signal being connected to said fluorescence per unit volume calculating means to refine the output thereof.

54. The apparatus recited in claim 53, and further comprising:

fourth detector means for sensing pressure and producing an output signal indicative thereof;

means connected to said output of said fourth detector means for producing as an output a fourth electrical signal representative of depth of said fourth detector, said fourth electrical signal being connected to said attenuation coefficient signal producing means to enable said attenuation coefficient signal to be further refined.

* * * * *